United States Patent [19]

Avery

[11] Patent Number: 4,887,466

[45] Date of Patent: Dec. 19, 1989

[54] WET BULB SENSOR SYSTEM

[76] Inventor: Gil Avery, P.O. Box 341165, Memphis, Tenn. 38184

[21] Appl. No.: 186,459

[22] Filed: Apr. 26, 1988

Related U.S. Application Data

[63] Continuation-in-part of Ser. No. 100,171, Sep. 23, 1987, abandoned.

[51] Int. Cl.[4] .......................................... G01N 25/62
[52] U.S. Cl. ........................................ 73/338; 73/335
[58] Field of Search ................ 73/335, 338, 19, 338.6; 374/109

[56] References Cited

U.S. PATENT DOCUMENTS

| | | | |
|---|---|---|---|
| 1,620,864 | 3/1927 | Benesh | 73/338.6 |
| 1,942,934 | 1/1934 | Reeve | 73/335 |
| 2,156,162 | 4/1939 | Pfening et al. | 73/338 |
| 2,302,529 | 11/1942 | Conklin | 73/338.6 |
| 2,427,931 | 9/1947 | Spanner | 73/338.6 |
| 3,191,313 | 6/1965 | Moorhouse et al. | 73/338 |
| 4,013,038 | 3/1977 | Rogers et al. | 73/338 |
| 4,461,167 | 7/1984 | Kent et al. | 73/338 |
| 4,559,823 | 12/1985 | Rosen et al. | 73/338 |

FOREIGN PATENT DOCUMENTS

| | | | |
|---|---|---|---|
| 3546364 | 7/1986 | Fed. Rep. of Germany | 73/338 |
| 96235 | 8/1981 | Japan | 73/338 |
| 1144042 | 3/1985 | U.S.S.R. | 73/338 |
| 587307 | 11/1946 | United Kingdom | 73/338 |

Primary Examiner—Hezron E. Williams
Attorney, Agent, or Firm—Walker & McKenzie

[57] ABSTRACT

A wet bulb sensor system for taking the wet bulb temperature of air. The sensor system includes an air passageway, a fan for drawing the air into and through the passageway, a filter disposed adjacent the intake of the air passageway, a temperature sensor for determining the temperature of air, a wet bulb sump opening upwardly into the passageway, a tank holding a quantity of replenishment water, a wick surrounding the lower end of the temperature sensor and extending into the sump, a water conduit communicating the tank with the sump, and an air conduit communicating the air space above the water in the sump with the space in the tank above the water therein. A second embodiment does not have the air conduit communicating the air space above the sump with the air space in the tank, but instead has a pressure sensor operatively coupled to the tank for increasing the air pressure in the tank to force the water to an operating level in the sump when the fan is operating, and for decreasing the air pressure in the tank to cause the water in the sump to drop below the wick when the fan is not operating. A modified arrangement of the wick is provided wherein the wick extends lengthwise along a sufficient portion of the length of the air passageway to pre-cool the air and water in the wick to the thermodynamic wet bulb temperature of the air flowing through the air passageway.

14 Claims, 3 Drawing Sheets

WET BULB SENSOR SYSTEM

CROSS-REFERENCE TO RELATED APPLICATION

This is a continuation-in-part of my application, Ser. No. 100,171 now abandoned, filed Sept. 23, 1987 entitled "Wet Bulb Sensor System."

BACKGROUND OF THE INVENTION

1. Field of the Invention:

The present invention relates in general to sensors for determining the wet bulb temperature of air.

2. Description of the Related Art:

Various wet bulb sensors have been heretofore developed for determining the wet bulb temperature of the air. Some of the problems of previous sensors are: Most of the prior sensors used city water and because of the hardness of much of the water, the wicks in the wet bulb sensors became dirty and clogged up with various contaminants such as the lime in the water. Consequently, the dirty wicks prevented the wet bulb sensors from recording the wet bulb temperature properly. In the wet bulb sensors which used distilled water to overcome the contamination problem, it was too expensive due to the evaporation of the costly distilled water. A preliminary patentability search conducted in class 73, subclasses 335 and 338, disclosed the following patents: Stahlberg, U.S. Pat. No. 3,157,049; Okey, U.S. Pat. No. 2,143,795; Grasso et al, U.S. Pat. No. 3,712,140; Conklin, U.S. Pat. No. 2,302,528; Miller, U.S. Pat. No. 3,253,465; and Bauer, U.S. Pat. No. 3,886,797. None of the above patents disclose or suggest the present invention.

SUMMARY OF THE INVENTION

The present invention is directed toward providing an improved wet bulb sensor system which overcomes the above-mentioned and other problems. The concept of the present invention is to provide a unique combination of components in which a filter is used to filter the air so that the air that goes over the wick is clean, in which only distilled water is used, in which a tank for the distilled water is connected to the wet bulb sump by a conduit for replenishing the water in the sump, and in which only a very small quantity of air is used to flow across the wick so that the amount of evaporation is minimized.

One of the objectives of the present invention is to provide a means in such a wet bulb system for maintaining the water in the wet bulb sump at the proper height in the event of a change in pressure in the air chamber in the space above the sump due to a dirty filter or for any other reason.

Another objective of the present invention is to provide means for separating the wick from the water in the wet bulb sump when the fan in the system is stopped, so that the amount of evaporation of water from the wet bulb sump is reduced.

Another objective of the present invention is to provide a pre-cooling portion of the wick extending lengthwise along a sufficient portion of the length of the air passageway to pre-cool the air and water in the wick to the thermodynamic wet bulb temperature of the air flowing through the air passageway.

DESCRIPTION OF THE PREFERRED EMBODIMENT

Figure 1:
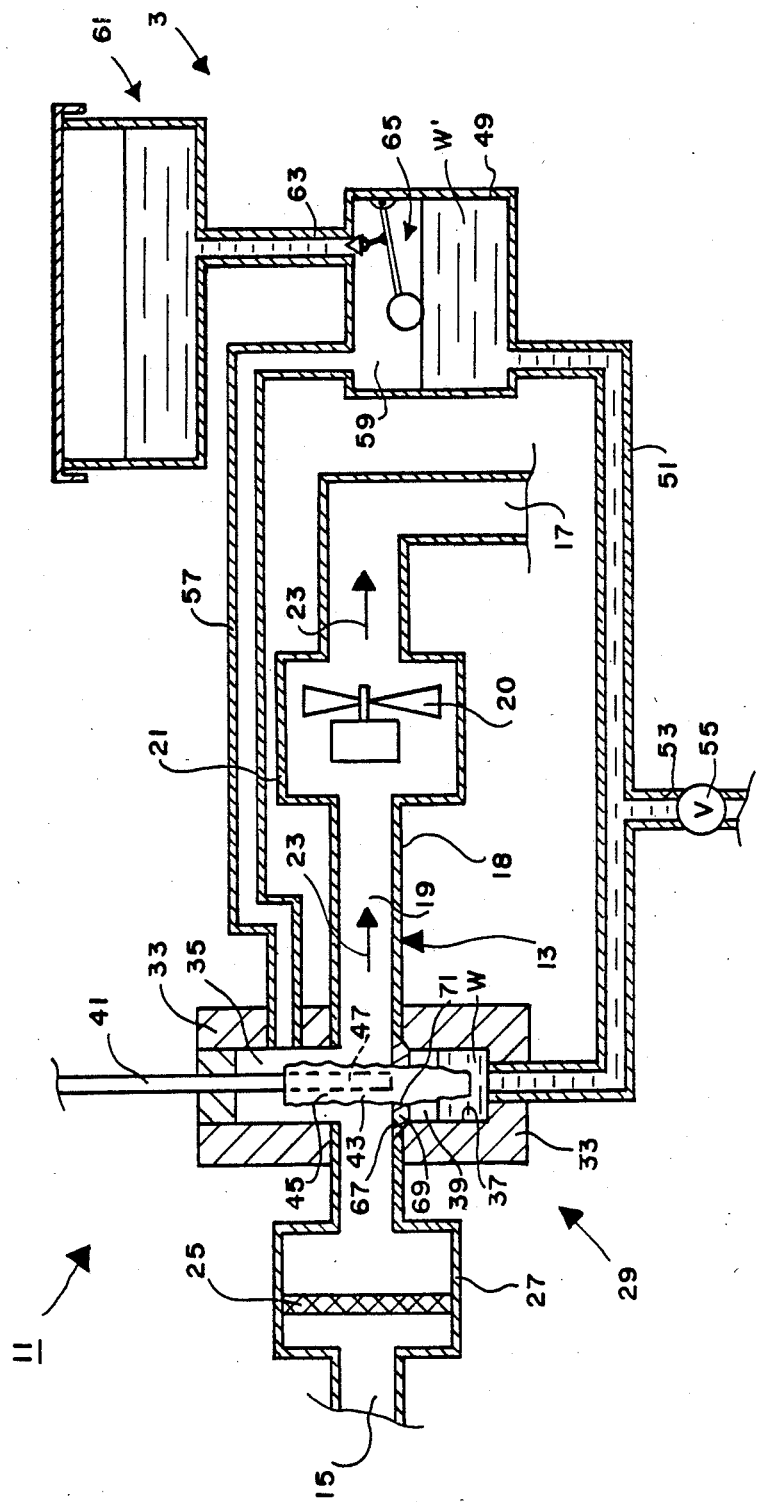
FIG. 1 is a diagrammatic view of a preferred embodiment of the wet bulb system of the present invention.

The preferred embodiment of the wet bulb sensor system 11 of the present invention is shown in FIG. 1 and includes an air passageway means 13 having an air intake 15 for introducing air into the passageway means for the wet bulb temperature of the air to be determined and having an air exhaust 17 for exhausting the air after the wet bulb temperature has been taken. The specific construction, size and material of air passageway means 13 may vary as will now be apparent to those skilled in the art. Thus, for example, it may be in the form of a conduit 18 of aluminum or the like defining in the interior thereof the air passageway 19 of air passageway means 13.

It will be understood by those skilled in the art that the air to be sampled for its wet bulb temperature may be directed to the air intake 15 by suitable well-known means, not shown, such as conduits leading from the outside atmosphere or selected area to be sampled.

A fan 20 is disposed in an enlarged portion 21 of air passageway means 13 between intake 15 and exhaust 17 to draw the air into intake 15 and move it through the air passageway 19 in the direction shown by the arrows 23 and out the exhaust 17. Fan 20 is preferably an electrical fan of any construction known to those skilled in the art, driven by a suitable source of electricity, and controlled by well-known controllers or switches not shown. The amount of air moved by the fan 20 is preferably about 2 cfm (two cubic feet per minute) or less.

System 11 includes filter means 25 disposed in an enlarged portion 27 of passageway means 13 downstream of intake 15 for filtering the air entering at intake 15 and flowing through passageway 19. Filter means 25 is of any suitable construction well known to those skilled in the art for cleaning the air of contamination which might be harmful to the wet bulb sensor system 11 and is preferably of the well-known removable type which is suitably supported in enlarged portion 27 by well-known means.

System 11 includes a wet bulb sensor assembly 29 and a water replenishment means 31 for replenishing the water in the wet bulb sensor assembly.

Wet bulb sensor assembly 29 is disposed in system 11 between intake 15 and fan 20 and includes an enclosed housing 33 mounted on the exterior of conduit 18 by suitable well-known means. Housing 33 is hollow and defines an air chamber 35 in the upper interior thereof and defines a wet bulb sump 37 in the lower interior thereof for containing water W. Air chamber 35 opens downwardly into communication with passageway 19, and sump 37 opens upwardly into communication with passageway 19 so that the air pressure in air chamber 35 is substantially the same as the air pressure in the space 39 defined by the sump 37 above the water W in the sump.

Wet bulb sensor assembly 29 also includes temperature sensor means, which is preferably in the form of a thermometer or temperature sensor 41 well known to those skilled in the art. In addition, wet bulb sensor assembly 29 includes a wick 43 adjacent temperature sensor 41. Wick 43 is preferably in the form of a sleeve with the upper end portion 45 of the wick surrounding the lower end portion 47 of temperature sensor 41. Wick 43 normally extends downwardly beyond the end portion 47 of the temperature sensor 41 into the water W, which keeps the wick moist. The end portion 45 of the wick 43 and the end portion 47 of the temperature sensor 41 are disposed in passageway 19 between filter means 25 and fan 20 in the path of air flow through passageway 19 so that the temperature sensor 41 will indicate the wet bulb temperature of the air, as will now be understood by those skilled in the art.

Water replenishment means 31 includes a tank 49 holding a quantity of replenishment water W' to replenish the water in sump 37 as the water W evaporates in the sump. A conduit 51 extends from the interior of tank 49 adjacent the bottom thereof to the interior of sump 37 adjacent the bottom thereof for serving as a channel for the water W' to flow from tank 49 to sump 37 for the replenishment of the water in the sump. A drain pipe 53 is preferably provided in communication with the interior of conduit 51 for draining tank 49 and sump 37, if desired. Also, a valve 55 is provided in conduit 51.

Wet bulb sensor system 11 includes an air conduit 57 extending from the air chamber 35 to the interior of tank 49 adjacent the top thereof to communicate space 39 above water W with the space 59 above the water W' in tank 49 for balancing the air pressure in spaces 39, 59. As will now be understood by those skilled in the art, this balancing of the pressures will cause the water levels in sump 37 and tank 49 to be the same.

In addition, wet bulb sensor system 11 preferably includes a clean water supply 61, well known to those skilled in the art, communicating with tank 49 through a pipe 63. Also, a float valve assembly 65, well known to those skilled in the art, is preferably provided to control the amount of water introduced into tank 49 from clean water supply 61 and to control the level of water W' in tank 49 at a desired level.

If desired, the upper end of sump 37 may be provided with a tapered seat 67 removably receiving an adapter plate 69 seated thereon. Adapter plate 69 is provided with an opening 71 through the center thereof through which wick 43 extends. The opening 71 loosely receives the wick 43 so that the air on either side thereof is equalized whereby the air pressure in passageway 19 above the plate 69, as well as the air pressure in air chamber 35, is the same as the air pressure in space 39. Also, it will be understood that adapters having various sizes of openings 71 may be utilized for accommodating various sizes of wicks.

In the operation of the wet bulb sensor system 11, it will be understood that after introducing the water W' into tank 49 from clean water supply 61, the fan 20 is started and the air from the space to be tested for the wet bulb temperature thereof is drawn into passageway 19. The air then passes over the temperature sensor 41 and wick 43 which causes a certain amount of the water in wick 43 to evaporate depending upon the amount of water in the air being tested which in turn cools the temperature sensor and which then indicates the wet bulb temperature, as will now be apparent to those skilled in the art.

It will be understood that with the use of the wet bulb system 11 of the present invention, the air that flows over the wick 43 is clean since it is filtered by filter 25 which keeps the wick clean; and the water W is clean since it is distilled water, thereby keeping the wick free of contamination. In addition, it will be understood that the amount of evaporation is kept at a minimum since the system 11 uses a very small amount of air, and if desired, evaporation may be further reduced with the use of the adapter plate 69. Also, it will be understood that when the filter 25 becomes dirty which causes a drop in pressure across the filter and thus a negative pressure in passageway 19 and space 39, with the use of the present invention the water will not be drawn up into the air passageway 19 since the air conduit 57 balances the air pressure in spaces 39 and 59. It will be understood that the drawing of water into the passageway 19, which could otherwise occur without the system of the present invention, creates an undesirable condition that could damage the fan 20 and possibly cause other problems. Further, it will be understood that the undesirable problems created by an increase or decrease in the air pressure in the space 39 caused by various conditions, such as a change in the length or size of the conduits leading to the air intake 15, are alleviated by the use of the present invention.

Figure 2:
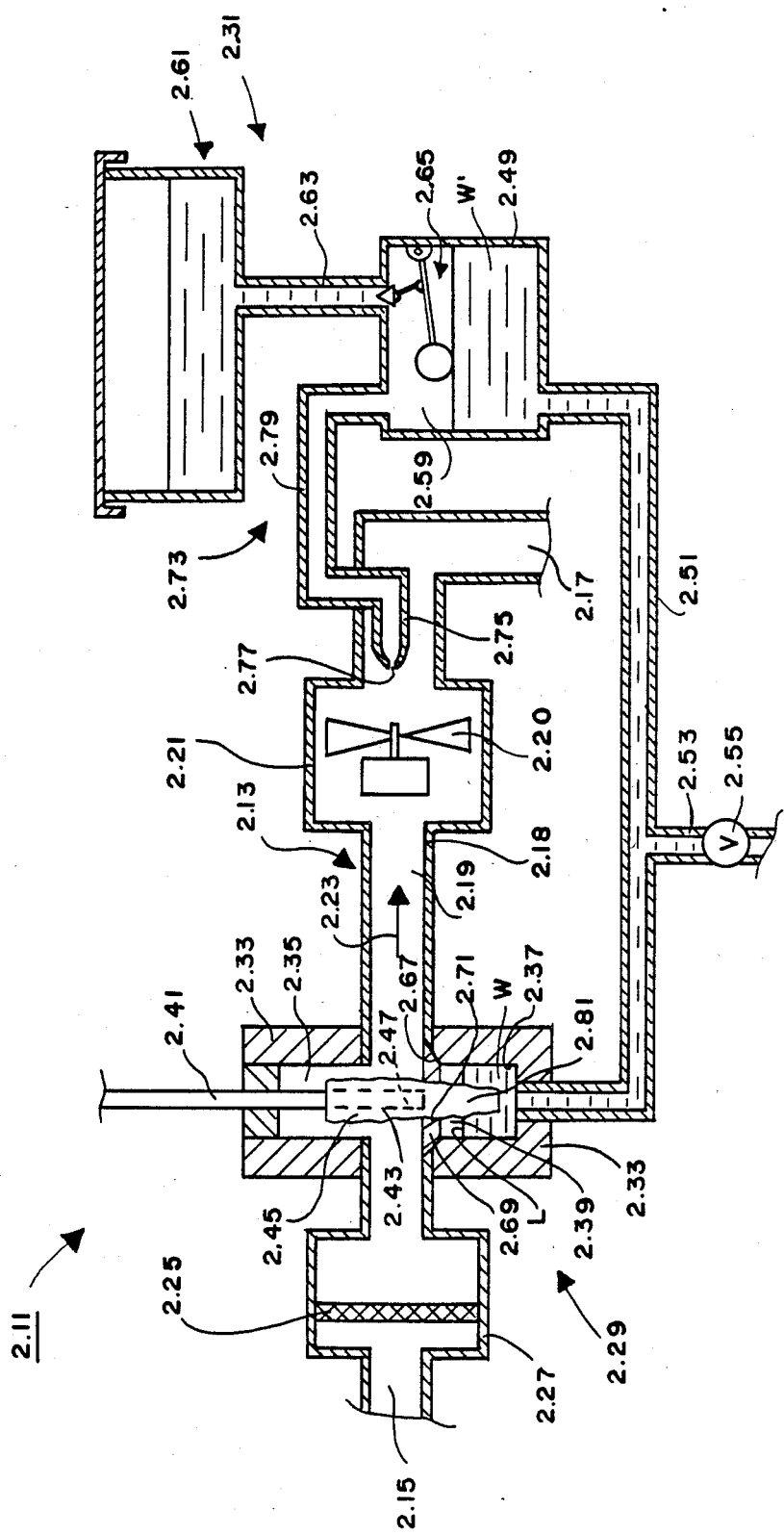
FIG. 2 is a diagrammatic view of a second emboidment of the wet bulb system of the present invention.

A second embodiment of the wet bulb sensor system of the present invention is shown in FIG. 2 and identified by the numeral 2.11. In many respects system 2.11 is similar to system 11 and similar parts have corresponding numbers except that the numbers begin with the number "2" followed by a decimal and a suffix having the same number as the corresponding part of system 11. Thus, wet bulb sensor system 2.11 comprises in general an air passageway means 2.13 having an air intake 2.15 for introducing air into the passageway means for the wet bulb temperature of the air to be determined and having an air exhaust 2.17 for exhausting the air after the wet bulb temperature has been taken. The specific construction, size and material of air passageway means 2.13 may vary as will now be apparent to those skilled in the art. Thus, for example, it may be in the form of a conduit 2.18 of aluminum or the like defining in the interior thereof the air passageway 2.19 of air passageway means 2.13.

It will be understood by those skilled in the art that the air to be sampled for its wet bulb temperature may be directed to the air intake 2.15 by suitable well-known means, not shown, such as conduits leading from the outside atmosphere or selected area to be sampled.

A fan 2.20 is disposed in an enlarged portion 2.21 of air passageway means 2.13 between intake 2.15 and exhaust 2.17 to draw the air into intake 2.15 and move it through the air passageway 2.19 in the direction shown by the arrow 2.23 and out the exhaust 2.17. Fan 2.20 is preferably an electrical fan of any construction known to those skilled in the art, driven by a suitable source of electricity, and controlled by well-known controllers or switches not shown. The amount of air moved by the fan 2.20 is preferably about 2 cfm (two cubic feet per minute) or less.

System 2.11 includes filter means 2.25 disposed in an enlarged portion 2.27 of passageway means 2.13 downstream of intake 2.15 for filtering the air entering at intake 2.15 and flowing through passageway 2.19. Filter means 2.25 is of any suitable construction well known to those skilled in the art for cleaning the air of contamination which might be harmful to the wet bulb sensor system 2.11 and is preferably of the well-known removable type which is suitably supported in enlarged portion 2.27 by well-known means.

System 2.11 includes a wet bulb sensor assembly 2.29 and a water replenishment means 2.31 for replenishing the water in the wet bulb sensor assembly.

Wet bulb sensor assembly 2.29 is disposed in system 2.11 between intake 2.15 and fan 2.20 and includes an enclosed housing 2.33 mounted on the exterior of conduit 2.18 by suitable well-known means. Housing 2.33 is hollow and defines an air chamber 2.35 in the upper interior thereof and defines a wet bulb sump 2.37 in the lower interior thereof for containing water W. Air chamber 2.35 opens downwardly into communication with passageway 2.19, and sump 2.37 opens upwardly into communication with passageway 2.19 so that the air pressure in air chamber 2.35 is substantially the same as the air pressure in the space 2.39 defined by the sump 2.37 above the water W in the sump.

Wet bulb sensor assembly 2.29 also includes temperature sensor means, which is preferably in the form of a thermometer or temperature sensor 2.41 well known to those skilled in the art. In addition, wet bulb sensor assembly 2.29 includes a wick 2.43 adjacent temperature sensor 2.41. Wick 2.43 is preferably in the form of a sleeve with the upper end portion 2.45 of the wick surrounding the lower end portion 2.47 of temperature sensor 2.41. Wick 2.43 normally extends downwardly beyond the end portion 2.47 of the temperature sensor 2.41 into the water W, which keeps the wick moist. The end portion 2.45 of the wick 2.43 and the end portion 2.47 of the temperature sensor 2.41 are disposed in passageway 2.19 between filter means 2.25 and fan 2.20 in the path of air flow through passageway 2.19 so that the temperature sensor 2.41 will indicate the wet bulb temperature of the air, as will now be understood by those skilled in the art.

Water replenishment means 2.31 includes a tank 2.49 holding a quantity of replenishment water W' to replenish the water in sump 2.37 as the water W evaporates in the sump. A conduit 2.51 extends from the interior of tank 2.49 adjacent the bottom thereof to the interior of sump 2.37 adjacent the bottom thereof for serving as a channel for the water W' to flow from tank 2.49 to sump 2.37 for the replenishment of the water in the sump. A drain pipe 2.53 is preferably provided in communication with the interior of conduit 2.51 for draining tank 2.49 and sump 2.37, if desired. Also, a valve 2.55 is provided in conduit 2.51. In addition, wet bulb sensor system 2.11 preferably includes a clean water supply 2.61, well known to those skilled in the art, communicating with tank 2.49 through a pipe 2.63. Also, a float valve assembly 2.65, well known to those skilled in the art, is preferably provided to control the amount of water introduced into tank 2.49 from clean water supply 2.61 and to control the level of water W' in tank 2.49 at a desired level.

If desired, the upper end of sump 2.37 may be provided with a tapered seat 2.67 removably receiving an adapter plate 2.69 seated thereon. Adapter plate 2.69 is provided with an opening 2.71 through the center thereof through which wick 2.43 extends. The opening 2.71 loosely receives the wick 2.43 so that the air on either side thereof is equalized whereby the air pressure in passageway 2.19 above the plate 2.69 as well as the air pressure in air chamber 2.35 is the same as the air pressure in space 2.39. Also, it will be understood that adapters having various sizes of openings 2.71 may be utilized for accommodating various sizes of wicks.

The differences between wet bulb sensor system 11 and wet bulb sensor system 2.11 are described hereinafter. In system 2.11 the air conduit 57 is omitted and instead a pressure sensing means 2.73 is provided for increasing the air pressure in the space 2.59 in tank 2.49 above the water W' therein to force the water W to an operating level L in sump 2.37 when fan 2.20 is operating and for decreasing the air pressure in space 2.59 to cause the water W in sump 2.37 to drop below wick 2.43 when fan 2.20 is not operating.

More specifically, pressure sensing means 2.73 includes an air pressure sensing tube 2.75, well known to those skilled in the art. Pressure sensing tube 2.75 is disposed in air passageway 2.19 downstream of fan 2.20 with the open end 2.77 of sensing tube 2.75 facing toward the fan 2.20. Pressure sensing tube 2.75 is operatively connected to the space 2.59 by a conduit 2.79 which extends from the tube 2.75 to the upper interior of tank 2.49 above water W'. The parts including the size of sump 2.37, the pressure in tank 2.49, etc. are so coordinated, as will now be understood by those skilled in the art, that when the fan 2.20 is operating, the water W is at the operating level L which is below the passageway 2.19, and when the fan is not operating, the level of water W is below wick 2.43.

More specifically, in the operation of wet bulb sensor system 2.11, when fan 2.20 is on, the discharge therefrom creates a positive pressure on the sensing tube 2.75 which is communicated to the space 2.59 by the conduit 2.79. The positive pressure in space 2.59 forces the water W in sump 2.37 up to the operating level L. Then, when the fan 2.20 is turned off, the water W drops down below the lower end 2.81 of wick 2.43. Thus, since the wick 2.43 does not absorb the water, water is conserved during the off periods of the fan 2.20. The operation of the remainder of the components of system 2.11 is substantially the same as the operation of system 11 and reference should be made to the previous description of the operation of system 11 for a more detailed description of such components.

Figure 3:
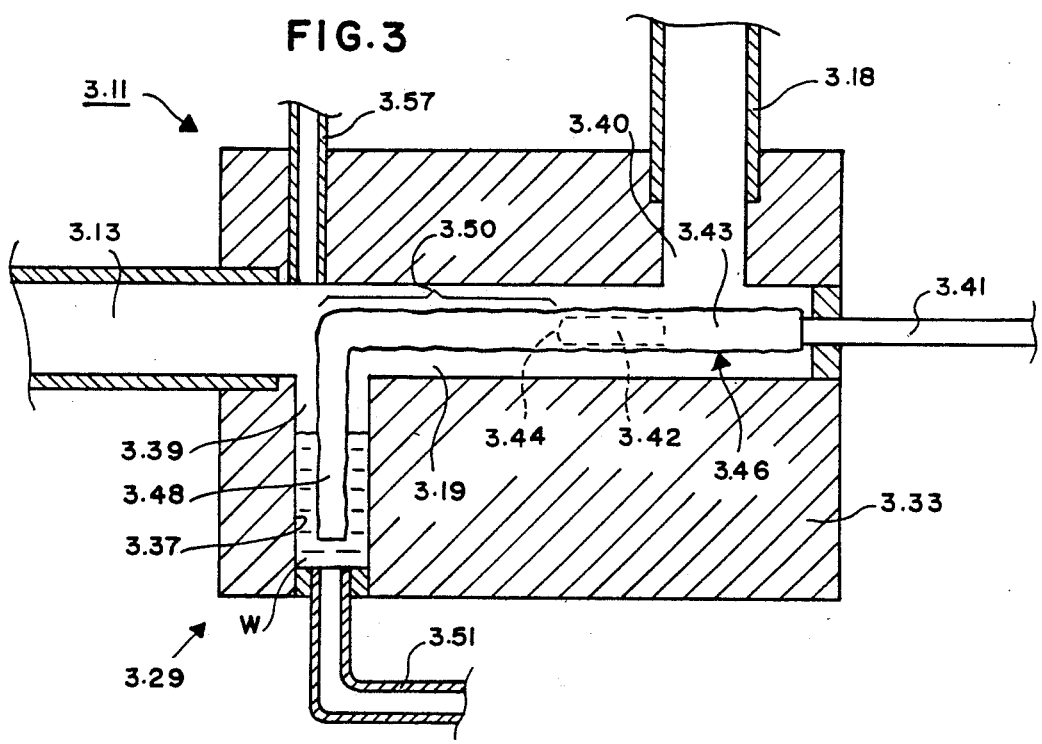
FIG. 3 is a diagrammatic view of a modification of a portion of the embodiment of FIG. 1 of the wet bulb system of the present invention.

A modification of a portion of the system 11 is shown in FIG. 3. In this modified system 3.11 similar parts to those of FIG. 1 have corresponding numbers except that the numbers begin with the number "3" followed by a decimal and a suffix having the same number as the corresponding part of system 11. Thus, a modified arrangement of wick 3.43 is provided, which will be better understood in the description to follow. Also, the housing 3.33 is arranged somewhat differently from housing 33, as will be seen from a comparison of FIGS. 3 and 1. It will be noted in such a comparison that air passageway means 3.13 is defined in part by the air passageway 3.19 provided horizontally through housing 3.33 and in part by a vertical portion 3.40 which communicates with the horizontal portion of air passageway 3.19 and extends upwardly therefrom where it communicates with the end of conduit 3.18.

As in the system shown in FIG. 1, the modified system 3.11 has a wet bulb sump 3.37 provided in housing 3.33 for containing water W. Sump 3.37 opens upwardly into communication with air passageway 3.19, and air conduit 3.57 is in communication with air passageway 3.19 above sump 3.37. Conduit 3.51 communicates with the interior of sump 3.37 adjacent the bottom thereof.

Wet bulb sensor assembly 3.29 includes temperature sensor means, which is preferably in the form of a thermometer or temperature sensor 3.41 having an elongated sensitive portion 3.42 along one end thereof terminating in a distal end 3.44 well known to those skilled in the art. In addition, wet bulb sensor assembly 3.29 includes wick 3.43 having a first end 3.46 and a second end 3.48. First end 3.46 of wick 3.43 is adjacent sensitive portion 3.42 of temperature sensor 3.41. Wick 3.43 extends beyond distal end 3.44 to define an elongated pre-cooling portion, shown by the bracket 3.50, of wick 3.43 and the second end 3.48 extends into wet bulb sump 3.37 for keeping sensitive portion 3.42 of temperature sensor 3.41 moist with water.

The remainder of system 3.11, not shown in FIG. 3, operates in the same manner and is of the same construction as system 11. Thus, conduit 3.18 leads to a fan corresponding to fan 20, conduit 3.51 connects to a tank, corresponding to tank 49, adjacent the bottom thereof, air conduit 3.57 connects to the interior of the tank, not shown, corresponding to tank 49, adjacent the top thereof to communicate space 3.39 above water W with the space above the water in the tank, not shown, corresponding to tank 49 for balancing the two spaces in the same manner as spaces 39 and 59 are balanced in system 11, and passageway means 3.13 connects to an enlarged portion corresponding to enlarged portion 27. Also, other structure is provided as in system 11 of like construction and similar operation corresponding to exhaust 17, enlarged portion 21, filter means 25, drain pipe 53, valve 55, clean water supply 61, pipe 63, float valve assembly 65, and water replenishment means 31. In addition, if desired, the upper end of sump 3.37 may be provided with a tapered seat, not shown, removably receiving an adapter plate and having an opening, not shown, corresponding respectively to tapered seat 67, adapter plate 69 and opening 71 of system 11 with the opening loosely receiving the second end 3.48 of wick 3.43.

From the foregoing, it will be understood that the sensitive portion 3.42 of temperature sensor 3.41 and wick 3.43 are disposed in air passageway means 3.13 between a filter means, not shown, corresponding to filter means 25 of system 11 and a fan, not shown, corresponding to fan 20 of system 11, in the path of flow of the air with pre-cooling portion 3.50 of wick 3.43 extending lengthwise along a sufficient portion of the length of air passageway means 3.13 to pre-cool the air and water in wick 3.43 to the thermodynamic wet bulb temperature of the air flowing through air passageway means 3.13.

Figure 4:
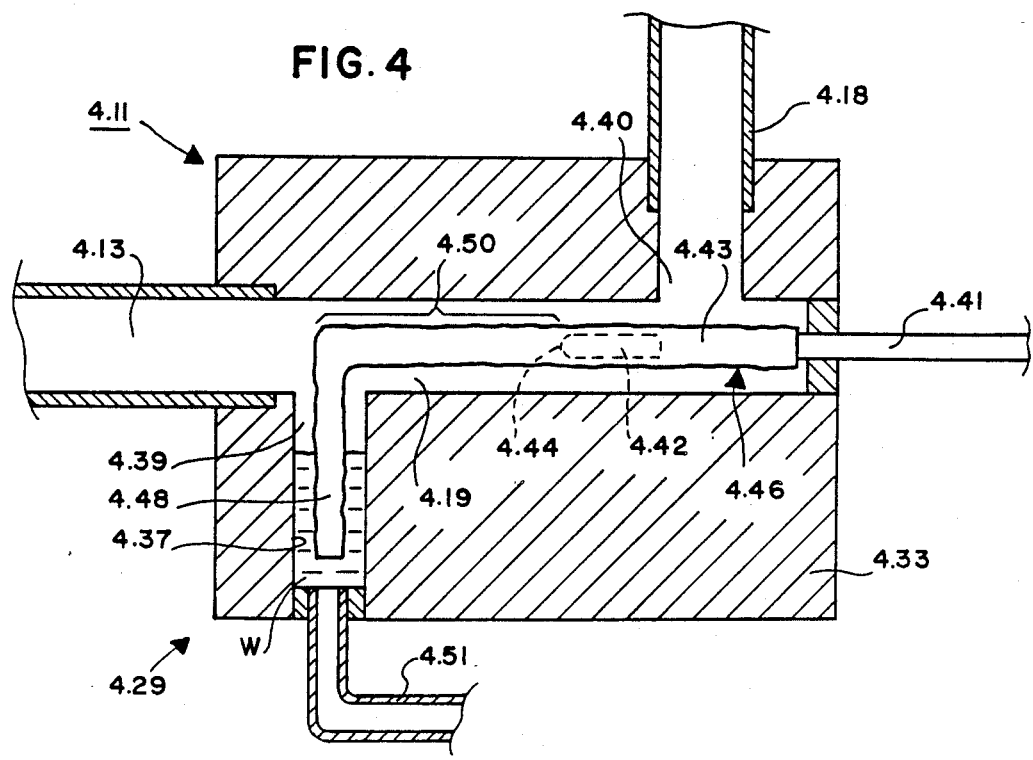
FIG. 4 is a diagrammatic view of a modification of a portion of the embodiment of FIG. 2 of the wet bulb system of the present invention.

A modification of a portion of the system 2.11 is shown in FIG. 4. In this modified system 4.11, similar parts to those of FIGS. 3 and 2 have corresponding numbers except that the numbers begin with the number "4" followed by a decimal and a suffix having the same number as the corresponding parts of systems 3.11 and 2.11. Thus, the following parts of system 4.11 are of the same structure and function as the corresponding parts of system 3.11: wick 4.43, housing 4.33, air passageway means 4.13, air passageway 4.19, vertical portion 4.40, conduit 4.18, space 4.39, wet bulb sensor assembly 4.29, temperature sensor 4.41, sensitive portion 4.42, distal end 4.44 of sensitive portion 4.42, first end 4.46 of wick 4.43, second end 4.48 of wick 4.43, pre-cooling portion 4.50, and water conduit 4.51. As in FIG. 2, there is no air conduit in system 4.11 corresponding to air conduit 57 or 3.57.

The remainder of system 4.11, not shown in FIG. 4, operates in the same manner and is of the same construction as system 2.11. Thus, conduit 4.18 leads to a fan corresponding to fan 2.20, conduit 4.51 connects to a tank, corresponding to tank 2.49, adjacent the bottom thereof, and passageway means 4.13 connects to an enlarged portion corresponding to enlarged portion 2.27. Also, other structure is provided as in system 2.11 of like construction and similar in operation corresponding to exhaust 2.17, enlarged portion 2.21, filter means 2.25, drain pipe 2.53, valve 2.55, clean water supply 2.61, pipe 2.63, float valve assembly 2.65, and water replenishment means 2.31. In addition, if desired, the upper end of sump 4.37 may be provided with a tapered seat, not shown, removably receiving an adapter plate and having an opening, not shown, corresponding respectively to tapered seat 2.67, adapter plate 2.69 and opening 2.71 of system 2.11 with the opening loosely receiving the second end 4.48 of wick 4.43.

Although the present invention has been described and illustrated with respect to a preferred embodiment and a preferred use therefor, and modifications thereof, it is not to be so limited since modifications and changes can be made therein which are within the full intended scope of the invention.

I claim:

1. A wet bulb sensor system for taking the wet bulb temperature of air, said system comprising:
   (a) air passageway means having an air intake for introducing air into said passageway means for the wet bulb temperature of the air to be determined, said passageway means having an air exhaust;
   (b) fan means in said passageway means for drawing the air into said passageway means through said air intake and for causing the air to flow through said passageway means and out said exhaust;
   (c) filter means disposed in said passageway means for filtering the air flowing through said passageway means;
   (d) temperature sensor means for determining the temperature of air;
   (e) an enclosed housing means having an interior, said housing defining an air chamber and a wet bulb sump in the interior thereof, said wet bulb sump having an upper end opening into said passageway means for receiving a quantity of water therein, said air chamber being in communication with said passageway means and said wet bulb sump, and said wet bulb sump defining a space above the water therein;
   (f) wick means adjacent said temperature sensor means and extending into said wet bulb sump for keeping the temperature sensor moist with water;
   (g) said temperature sensor means and said wick means being disposed in said passageway means between said filter means and said fan means in the path of flow of the air for determining the wet bulb temperature of the air flowing through said passageway means;
   (h) tank means holding a quantity of replenishment water to replenish the water in said wet bulb sump as the water evaporates in said wet bulb sump, said tank means having a space above the water in said tank means, said space above the water in said tank means being closed to the ambient atmosphere; and
   (i) water conduit means communicating said tank means and said wet bulb sump for serving as a channel for the water to flow from said tank means to said wet bulb sump for the replenishment of the water in said wet bulb sump.

2. The wet bulb sensor system of claim 1 which includes an air conduit means communicating said air chamber with said space above the water in said tank means for balancing the air pressure in said air chamber and in the space above the water in said tank means to cause the water levels in said wet bulb sump and said tank means to be the same.

3. The wet bulb sensor system of claim 2 in which said upper end of said wet bulb sump is provided with a seat; and in which is included an adapter plate means removably seated on said seat for minimizing surface evaporation of the water in said wet bulb sump, said seat having an opening through which said wick means extends.

4. The wet bulb sensor system of claim 3 in which is included clean water supply means communicating with said tank means for supplying clean water to said tank means, and in which is included float valve means operatively coupled to said clean water supply means and said tank means for controlling the level of the water in said tank means and the amount of water introduced into said tank means from said clean water supply means.

5. The wet bulb sensor system of claim 4 in which the air flow through said passageway means is less than approximately 2 cubic feet per minute.

6. A wet bulb sensor system for taking the wet bulb temperature of air, said system comprising:
(a) air passageway means having an air intake for introducing air into said passageway means for the wet bulb temperature of the air to be determined, said passageway means having an air exhaust;
(b) fan means in said passageway means for drawing the air into said passageway means through said air intake and for causing the air to flow through said passageway means and out said exhaust;
(c) filter means disposed in said passageway means for filtering the air flowing through said passageway means;
(d) temperature sensor means for determining the temperature of air;
(e) an enclosed housing means having an interior, said housing defining an air chamber and a wet bulb sump in the interior thereof, said wet bulb sump having an upper end opening into said passageway means for receiving a quantity of water therein, said air chamber being in communication with said passageway means and said wet bulb sump, and said wet bulb sump defining a space above the water therein;
(f) wick means adjacent said temperature sensor means and extending into said wet bulb sump for keeping the temperature sensor moist with water;
(g) said temperature sensor means and said wick means being disposed in said passageway means between said filter means and said fan means in the path of flow of the air for determining the wet bulb temperature of the air flowing through said passageway means;
(h) tank means holding a quantity of replenishment water to replenish the water in said wet bulb sump as the water evaporates in said wet bulb sump, said tank means having a space above the water in said tank means;
(i) water conduit means communicating said tank means and said wet bulb sump for serving as a channel for the water to flow from said tank means to said wet bulb sump for the replenishment of the water in said wet bulb sump; and
(j) pressure sensing means having an inlet in said passageway means downstream of said fan means and operatively coupled to said tank means for increasing the air pressure in said tank means to force the water to an operating level in said wet bulb sump below said passageway means when said fan means is operating, and for decreasing the air pressure in said tank means to cause the water in said wet bulb sump to drop below said wick means when said fan means is not operating.

7. The wet bulb sensor system of claim 6 in which said upper end of said wet bulb sump is provided with a seat; and in which is included an adapter plate means removably seated on said seat for minimizing surface evaporation of the water in said wet bulb sump means, said seat having an opening through which said wick means extends.

8. The wet bulb sensor system of claim 7 in which is included clean water supply means communicating with said tank means for supplying clean water to said tank means, and in which is included float valve means operatively coupled to said clean water supply means and said tank means for controlling the level of the water in said tank means and the amount of water introduced into said tank means from said clean water supply means.

9. The wet bulb sensor system of claim 8 in which the air flow through said passageway means is less than approximately 2 cubic feet per minute.

10. A wet bulb sensor system for taking the wet bulb temperature of air, said system comprising:
(a) air passageway means having an air intake for introducing air into said passageway means for the wet bulb temperature of the air to be determined, said passageway means having an air exhaust;
(b) fan means in said passageway means for drawing the air into said passageway means through said air intake and for causing the air to flow through said passageway means and out said exhaust;
(c) filter means disposed in said passageway means for filtering the air flowing through said passageway means;
(d) temperature sensor means for determining the temperature of air, said temperature sensor means having an elongated sensitive portion along one end thereof terminating in a distal end thereof;
(e) an enclosed housing means having an interior, said housing defining a wet bulb sump in the interior thereof, said wet bulb sump having an upper end opening into said passageway means for receiving a quantity of water therein, and said wet bulb sump defining a space above the water therein;
(f) wick means having a first end and a second end, said first end of said wick means being adjacent said sensitive portion of said temperature sensor means and said second end of said wick means extending beyond said distal end of said sensitive portion to define a pre-cooling portion of said wick means and thence extending into said wet bulb sump for keeping said sensitive portion of said sensor means moist with water;
(g) said temperature sensor means and said wick means being disposed in said passageway means between said filter means and said fan means in the path of flow of the air with said pre-cooling portion of said wick means extending lengthwise along a sufficient portion of the length of said passageway means to pre-cool the air and water in said wick means to the thermodynamic wet bulb temperature of the air flowing through said passageway means;

(h) tank means holding a quantity of replenishment water to replenish the water in said wet bulb sump as the water evaporates in said wet bulb sump, said tank means having a space above the water in said tank means; and (i) water conduit means communicating said tank means and said wet bulb sump for serving as a channel for the water to flow from said tank means to said wet bulb sump for the replenishment of the water in said wet bulb sump.

11. The wet bulb sensor system of claim 10 which includes an air conduit means communicating said space above the water in said wet bulb sump with said space above the water in said tank means for balancing the air pressure in said space above the water in said wet bulb sump and in the space above the water in said tank means to cause the water levels in said wet bulb sump and said tank means to be the same.

12. The wet bulb sensor system of claim 11 in which the air flow through said passageway means is less than approximately 2 cubic feet per minute.

13. A wet bulb sensor system for taking the wet bulb temperature of air, said system comprising:

(a) air passageway means having an air intake for introducing air into said passageway means for the wet bulb temperature of the air to be determined, said passageway means having an air exhaust;

(b) fan means in said passageway means for drawing the air into said passageway means through said air intake and for causing the air to flow through said passageway means and out said exhaust;

(c) filter means disposed in said passageway means for filtering the air flowing through said passageway means;

(d) temperature sensor means for determining the temperature of air, said sensor means having an elongated sensitive portion along one end thereof terminating in a distal end thereof;

(e) an enclosed housing means having an interior, said housing defining a wet bulb sump in the interior thereof, said wet bulb sump having an upper end opening into said passageway means for receiving a quantity of water therein, and said wet bulb sump defining a space above the water therein;

(f) wick means having a first end and a second end, said first end of said wick means being adjacent said sensitive portion of said sensor means and said second end of said wick means extending beyond said distal end of said sensitive portion to define a pre-cooling portion of said wick means and thence extending into said wet bulb sump for keeping said sensitive portion of said sensor means moist with water;

(g) said temperature sensor means and said wick means being disposed in said passageway means between said filter means and said fan means in the path of flow of the air with said pre-cooling portion of said wick means extending lengthwise along a sufficient portion of the length of said passageway means to pre-cool the air and water in said wick means to the thermodynamic wet bulb temperature of the air flowing through said passageway means;

(h) tank means holding a quantity of replenishment water to replenish the water in said wet bulb sump as the water evaporates in said wet bulb sump, said tank means having a space above the water in said tank means;

(i) water conduit means communicating said tank means and said wet bulb sump for serving as a channel for the water to flow from said tank means to said wet bulb sump for the replenishment of the water in said wet bulb sump; and (j) pressure sensing means having an inlet in said passageway means downstream of said fan means and operatively coupled to said tank means for increasing the air pressure in said tank means to force the water to an operating level in said wet bulb sump below said passageway means when said fan means is operating, and for decreasing the air pressure in said tank means to cause the water in said wet bulb sump to drop below said wick means when said fan means is not operating.

14. The wet bulb sensor system of claim 13 in which the air flow through said passageway means is less than approximately 2 cubic feet per minute.

* * * * *